(12) United States Patent
Takita

(10) Patent No.: US 11,440,823 B2
(45) Date of Patent: Sep. 13, 2022

(54) METHOD FOR PRODUCING POLYHYDROXYALKANOIC ACID

(71) Applicant: KANEKA CORPORATION, Osaka (JP)

(72) Inventor: Masaki Takita, Takasago (JP)

(73) Assignee: KANEKA CORPORATION, Osaka (JP)

(*) Notice: Subject to any disclaimer, the term of this patent is extended or adjusted under 35 U.S.C. 154(b) by 931 days.

(21) Appl. No.: 16/311,536

(22) PCT Filed: Jun. 12, 2017

(86) PCT No.: PCT/JP2017/021597
§ 371 (c)(1),
(2) Date: Dec. 19, 2018

(87) PCT Pub. No.: WO2017/221755
PCT Pub. Date: Dec. 28, 2017

(65) Prior Publication Data
US 2019/0330089 A1    Oct. 31, 2019

(30) Foreign Application Priority Data
Jun. 23, 2016    (JP) .............................. JP2016-124460

(51) Int. Cl.
*C02F 3/34*        (2006.01)
*C02F 3/30*        (2006.01)
(Continued)

(52) U.S. Cl.
CPC ................ *C02F 3/34* (2013.01); *C02F 3/305* (2013.01); *C08G 63/90* (2013.01); *C02F 2101/16* (2013.01)

(58) Field of Classification Search
CPC ........ C02F 3/34; C02F 3/305; C02F 2101/16; C02F 3/341; C02F 3/26; C02F 3/301;
(Continued)

(56) References Cited

U.S. PATENT DOCUMENTS 5,798,440 A    8/1998    Liddell et al.
5,894,062 A    4/1999    Liddell
(Continued)

FOREIGN PATENT DOCUMENTS

EP    2 366 794 A1    9/2011
JP    7-79788 A    3/1995
(Continued)

OTHER PUBLICATIONS

Extended European Search Report dated Feb. 4, 2020 in European Patent Application No. 17815224.5, 8 pages.
(Continued)

*Primary Examiner* — Fred Prince
(74) *Attorney, Agent, or Firm* — Oblon, McClelland, Maier & Neustadt, L.L.P.

(57) ABSTRACT

An object of the present invention is to provide a method for producing PHA, which is capable of suppressing the cost of overall production equipment including a waste water treatment process in production of PHA using microorganisms. Provided is a method including: a production step of purifying or molding polyhydroxyalkanoic acid biosynthesized in bacterial cells of a microorganism; a discharge step of discharging waste water containing nitrogen-containing impurities from the production step; and a nitrogen removal step of biologically treating the waste water to remove the nitrogen-containing impurities from the waste water. In the method, the residual ratio of the polyhydroxyalkanoic acid in the production step is 99% by weight or less, and the waste water that is biologically treated in the nitrogen
(Continued)

removal step contains the polyhydroxyalkanoic acid in addition to the nitrogen-containing impurities.

15 Claims, 2 Drawing Sheets

(51) Int. Cl.
*C08G 63/90* (2006.01)
*C02F 101/16* (2006.01)
(58) Field of Classification Search
CPC ............ C02F 2101/163; C02F 2101/34; C02F 2209/02; C02F 2209/06; C02F 2209/22; C02F 3/302; C08G 63/90; Y02W 10/10; C12P 7/625
USPC ......... 528/271; 210/601, 612, 620, 903, 905
See application file for complete search history.

(56) References Cited

U.S. PATENT DOCUMENTS

| | | | |
|---|---|---|---|
| 6,245,537 | B1 | 6/2001 | Williams et al. |
| 10,662,451 | B2 * | 5/2020 | Sun .................. C12N 1/20 |
| 2005/0196827 | A1 | 9/2005 | Osakada et al. |
| 2011/0293938 | A1 | 12/2011 | Takita et al. |
| 2013/0029388 | A1 | 1/2013 | Werker et al. |
| 2016/0102326 | A1 | 4/2016 | Takita et al. |
| 2017/0233773 | A1 * | 8/2017 | Finnegan .................. C12N 1/20 435/147 |

FOREIGN PATENT DOCUMENTS

| | | | |
|---|---|---|---|
| JP | 7-509131 A | | 10/1995 |
| JP | 10-504460 A | | 5/1998 |
| JP | 2014-132831 A | | 7/2014 |
| WO | WO 2005/085461 A1 | | 9/2005 |
| WO | WO 2010/067543 A1 | | 6/2010 |
| WO | WO 2010/116681 A1 | | 10/2010 |
| WO | WO 2011/070544 A2 | | 6/2011 |
| WO | WO 2017/073304 A1 | | 5/2017 |
| WO | WO 2017/221755 A1 * | | 12/2017 |

OTHER PUBLICATIONS

Hiraishi, A. et al. "Application of polyhydroxyalkanoates for denitrification in water and wastewater treatment", Applied Microbiology and Biotechnology, XP055581998, vol. 61, No. 2, Jan. 14, 2003, pp. 103-109.

International Search Report dated Sep. 5, 2017 in PCT/JP2017/021597 filed Jun. 12, 2017.

* cited by examiner

METHOD FOR PRODUCING POLYHYDROXYALKANOIC ACID

TECHNICAL FIELD

The present invention relates to a method for producing polyhydroxyalkanoic acid, the method including biosynthesizing polyhydroxyalkanoic acid in bacterial cells of a microorganism.

BACKGROUND ART

Polyhydroxyalkanoic acid (hereinafter, abbreviated as PHA) is a thermoplastic polyester which is produced and accumulated as an energy storage substance in cells of many microbial species, and the polyhydroxyalkanoic acid has biodegradability. At present, non-petroleum-derived plastics attract attention due to the growing awareness of environmental issues, and among them, biodegradable plastics such as PHA, which are taken in circulation of substances in the nature and give degradation products that are not harmful, attract attention, and are strongly desired to come into practical use. In particular, PHA produced and accumulated in bacterial cells by microorganisms is supposed to have a reduced adverse effect on ecosystems because PHA is taken in carbon circulation processes in the nature.

PHA produced by a microorganism is normally accumulated in bacterial cells of the microorganism, and therefore for using PHA as a plastic, a process is necessary in which PHA is separated and recovered from the bacterial cells of the microorganism. Further, it is desired to increase the purity of PHA and reduce the content of contaminants such as bacterial cell constituent components after the PHA is recovered.

For example, Patent Literature 1 discloses a method in which microbial cells that have produced and accumulated PHA are subjected to biological treatment and chemical treatment, and then physical disruption treatment to recover high-purity PHA. Patent Literature 2 discloses a method in which PHA is treated with an oxidizing agent such as hydrogen peroxide or ozone to remove impurities derived from bacterial cells, and Patent Literatures 3 and 4 disclose a method in which PHA is dissolved in a specific solvent, and then recovering the PHA from the solution. Further, as a method for forming a PHA aggregate in a PHA-containing aqueous suspension liquid, Patent Literature 5 discloses a method in which a PHA-containing aqueous suspension liquid is adjusted to an acidic condition, and Patent Literature 6 discloses a method in which a PHA-containing aqueous suspension liquid is heated. As described above, techniques for purification of PHA have been progressively accumulated, and reported in many patents and articles.

On the other hand, for attaining production of PHA by microorganisms on a commercial scale, a waste water treatment process is important in addition to a culture step and a purification step. Since a medium to be used for microbial culture for producing PHA contains nitrogen components, waste water generated in a PHA production process contains a large amount of nitrogen components. Particularly, since the main component of PHA which is a product is carbon, the carbon/nitrogen ratio in waste water tends to be lower than the carbon/nitrogen ratio in the medium. Thus, in production of PHA, generated waste water contains an excessively large amount of nitrogen, and therefore a high nitrogen removal ability is required in the waste water treatment process.

The main component of nitrogen components contained in waste water is ammonia nitrogen. Biological treatment of ammonia nitrogen requires two steps: a step of oxidizing ammonia nitrogen into nitric acid (nitrification step) and a step of reducing nitric acid into nitrogen molecules and releasing the nitrogen molecules outside the system as a nitrogen gas (denitrification step). In the former step, i.e., the nitrification step, it is necessary to acclimatize special bacteria called nitrification bacteria, and since the bacteria slowly grow, it takes considerable time for acclimation, and the size of waste water treatment equipment tends to be increased for securing the retention time.

On the other hand, an ammonia stripping method is known as a method for physically and chemically treating ammonia nitrogen, but the method has the problem that energy cost increases because steam is used.

As described above, many reports have been made on purification of PHA, but studies have not been made in view of overall production equipment including waste water treatment. Thus, the ratio of cost of waste water treatment equipment in overall PHA production equipment has been extremely high.

CITATION LIST

Patent Literature

PTL 1: WO 2010/116681
PTL 2: U.S. Pat. No. 6,245,537
PTL 3: JP-T No. H10-504460
PTL 4: JP-A No. H07-79788
PTL 5: WO 2010/067543
PTL 6: JP-T No. H07-509131

SUMMARY OF INVENTION

Technical Problem

Studies have been heretofore made for improving the purity of PHA by removing impurities from PHA produced by microorganisms, but these studies are aimed at improving the purification degree and yield of PHA, and studies have not been made in view of overall production equipment including waste water treatment. Thus, there is the problem that when considering improvement of the purity of PHA in view of overall production equipment including waste water treatment, equipment cost increases in large-scale commercial production of PHA.

An object of the present invention is to provide a method for producing PHA, which is capable of suppressing the cost of overall production equipment including a waste water treatment process in production of PHA using microorganisms.

Solution to Problem

The present inventors have extensively conducted studies for achieving the above-described object, and resultantly found that when waste water generated in the process of causing microorganisms to produce PHA and purifying or molding the PHA contains PHA at the time of biologically treating ammonia nitrogen contained in the waste water, the nitrification rate and the nitrogen removal rate are improved. Further, the present inventors have found that the scale of waste water treatment equipment can be reduced by incorporation of part of PHA as a product in waste water, leading to completion of the present invention.

Specifically, the present invention relates to a method for producing polyhydroxyalkanoic acid, the method including: a production step of purifying or molding polyhydroxyalkanoic acid biosynthesized in bacterial cells of a microorganism; a discharge step of discharging waste water containing nitrogen-containing impurities from the production step; and a nitrogen removal step of biologically treating the waste water to remove the nitrogen-containing impurities from the waste water. In the method, a residual ratio of the polyhydroxyalkanoic acid in the production step is 99% by weight or less, and the waste water that is biologically treated in the nitrogen removal step contains the polyhydroxyalkanoic acid in addition to the nitrogen-containing impurities.

Preferably, the production step includes a step of disrupting a polyhydroxyalkanoic acid-containing microorganism by a physical, chemical or biological method and decomposing and/or removing impurities other than the polyhydroxyalkanoic acid to purify the polyhydroxyalkanoic acid.

Preferably, the nitrogen-containing impurities include a water-soluble or water-dispersible component formed by decomposing any one of a protein, a lipid and a nucleic acid derived from the microorganism in the purification step.

Preferably, the polyhydroxyalkanoic acid contained in the waste water discharged from the discharge step has a volume average particle size of 5000 μm or less. Preferably, a concentration of dissolved oxygen in the waste water that is treated in the nitrogen removal step is 1.5 ppm or more. Preferably, a temperature of the waste water that is treated in the nitrogen removal step is 10 degrees Celsius or higher and 60 degrees Celsius or lower. Preferably, the waste water that is treated in the nitrogen removal step has a pH of 3 or more and 10 or less.

Advantageous Effects of Invention

According to the present invention, a nitrification reaction essential for treatment of ammonia nitrogen is accelerated at the time of biological treatment of ammonia nitrogen contained in waste water generated in the process of causing microorganisms to produce PHA and purifying or molding the PHA. Thus, it is possible to downsize a nitrification tank. Further, since a nitrification reaction can be made to coexist with a denitrification reaction, the nitrification reaction and the denitrification reaction can be carried out in one tank. Therefore, it is also possible to reduce the number of tanks required for treatment of waste water. Further, since the nitrogen removal rate in waste water is improved, the retention time in the treatment tank can be shortened, so that the treatment tank can be downsized. Further, the nitrogen removal rate in waste water can be improved without adding another treatment step or adding additives. Thus, according to the present invention, the cost of waste water treatment equipment can be reduced, and as a result, the cost of overall production equipment for large-scale commercial production of PHA can be suppressed.

DESCRIPTION OF EMBODIMENTS

Figure 1:
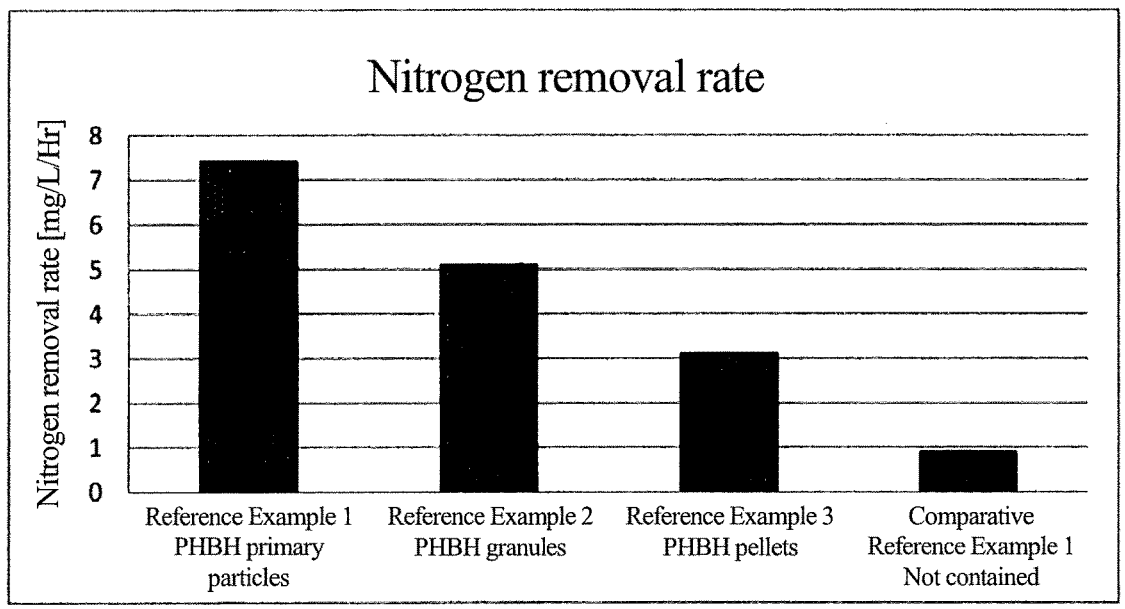
FIG. 1 illustrates graphs showing a nitrogen removal rate in the system for Reference Example 1-3 and Comparative Reference Example 1.

Hereinafter, the present invention will be described in more detail.

A method for producing PHA according to the present invention includes: a production step of purifying or molding polyhydroxyalkanoic acid (hereinafter, abbreviated as PHA) biosynthesized in bacterial cells of a microorganism; a discharge step of discharging waste water containing nitrogen-containing impurities from the production step; and a nitrogen removal step of biologically treating the waste water to remove the nitrogen-containing impurities from the waste water.

(PHA)

In the present invention, the PHA is a generic term of polymers having hydroxyalkanoic acid as a monomer unit. The hydroxyalkanoic acid is not particularly limited, and examples thereof include 3-hydroxybutyrate, 4-hydroxybutyrate, 3-hydroxyhexanonate, 3-hydroxypropionate, 3-hydroxyvalerate, 3-hydroxyhexanoate, 3-hydroxyheptanoate and 3-hydroxyoctanoate. These polymers may be homopolymers or copolymers containing two or more kinds of monomer units, and examples thereof include poly-3-hydroxybutyrate homopolymers, and poly-3-hydroxybutyrate copolymers such as poly-3-hydroxybutyrate-co-3-hydroxyhexanoate (PHBH), poly-3-hydroxybutyrate-co-3-hydroxyvalerate (PHBV) and poly-3-hydroxybutyrate-co-4-hydroxybutyrate. In the present invention, only one PHA, or a mixture of two or more PHAs may be produced.

(Production Step)

In the production step according to a preferred embodiment of the present invention, it is possible to carry out a step of culturing a microorganism capable of biosynthesizing PHA in bacterial cells, and a step of disrupting the microorganism by a physical, chemical or biological method and decomposing and/or removing impurities other than the PHA to purify the PHA. After the purification step, a molding step of molding the PHA into a desired shape can be carried out if necessary.

The PHA-producing microorganism for use in the present invention is not particularly limited as long as it is a microorganism capable of biosynthesizing PHA in bacterial cells. It is possible to use microorganisms isolated from the nature, microorganisms deposited at strain depository institutions (e.g., IFO and ATCC), mutants and transformants which can be prepared from these microorganisms, or the like. Examples thereof include bacteria such as *Cupriavidus, Alcaligenes, Ralstonia, Pseudomonas, Bacillus, Azotobacter, Nocardia* and *Aeromonas*. In particular, strains of *Alcaligenes lipolytica* (*A. lipolytica*), *Alcaligenes latus* (*A. latus*), *Aeromonas caviae* (*A. caviae*), *Aeromonas hydrophila* (*A. hydrophila*), *Cupriavidus necator* (*C. necator*) and the like are preferable. In addition, when the microorganism is not originally capable of producing PHA, or has a low PHA production capacity, a transformant obtained by introducing a target PHA synthase gene and/or a mutant thereof into the microorganism can also be used. The PHA synthase gene to be used for preparing such a transformant is not particularly limited, but a PHA synthase gene derived from *Aeromonas caviae* is preferable. By culturing the microorganism under appropriate conditions, a microorganism containing PHA in bacterial cells can be obtained. The method for culturing the microorganism is not particularly limited, and for example, the method described in JP-A No. H05-93049 is used.

After the culture step, a purification step of disrupting the microorganism (microorganism containing PHA (PHA-containing microorganism)) by a physical, chemical or biological method and decomposing and/or removing impurities other than the PHA to purify the PHA is carried out. The purification step is not particularly limited, and examples thereof include a step of performing enzyme treatment by adding an enzyme to a culture liquid or aqueous suspension liquid of a PHA-containing microorganism; a step of disrupting a PHA-containing microorganism by adding an acid or alkali to a culture liquid or aqueous suspension liquid of the PHA-containing microorganism; and a step of subjecting a PHA-containing microorganism to physical disruption treatment. The PHA-containing aqueous suspension liquid obtained by such treatment contains nitrogen-containing impurities. In this suspension liquid, PHA can be purified and isolated by separating the solid PHA from the aqueous phase.

If necessary, water can be added to the thus-isolated PHA to perform second purification, thereby further increasing the purity of the PHA. After the second purification, PHA is separated from the aqueous phase, whereby high-purity PHA can be isolated. The second purification can also be included in the purification step.

The PHA isolated by passing through the purification step can be dried, and then molded into various shapes as necessary. For example, the PHA can be molded into a sheet shape by performing melt pressing at 160° C., or molded into a pellet shape.

(Discharge Step)

The discharge step is a step of discharging waste water containing nitrogen-containing impurities from the production step. In the process for producing PHA, waste water containing nitrogen-containing impurities is generated mainly in the above-described purification step and molding step, but in the present invention, the waste water may be generated in any step, and is not particularly limited. In particular, much of the waste water containing nitrogen-containing impurities is generated in the purification step. In the purification step, the aqueous phase is separated from PHA, and in the discharge step, the aqueous phase is discharged as waste water. The discharged waste water is fed to a waste water treatment tank.

Most of nitrogen-containing impurities contained in waste water are components derived from the cultured microorganism, and include water-soluble or water-dispersible components formed by decomposing a protein, a lipid, a nucleic acid and the like in the purification step.

According to the production method of the present invention, the residual ratio of PHA in the production step is 99% by weight or less, and the waste water contains PHA in addition to the nitrogen-containing impurities. In a conventional production method, PHA as a product is adjusted so as not to be discharged from a production process (i.e., the residual rate is 100% by weight) for improvement of the yield, whereas the method of the present invention is characterized in that part of PHA (1% by weight or more based on the total amount of produced PHA) is discharged in waste water. Since waste water contains nitrogen-containing impurities and PHA, the rates of the nitrification reaction and the denitrification reaction of nitrogen-containing impurities in the subsequent nitrogen removal step can be improved to efficiently remove the nitrogen-containing impurities from the waste water.

Here, the residual ratio of PHA is a ratio of the weight of a PHA product obtained by passing through the purification and/or molding steps to the weight of PHA biosynthesized by culturing a microorganism. When the residual ratio is more than 99% by weight, the amount of PHA contained in waste water decreases, and therefore it is difficult to obtain an effect of the present invention, i.e., improvement of the nitrogen removal rate by incorporation of PHA. The residual ratio is preferably 99% by weight or less, more preferably 98% by weight or less, and still more preferably 97% by weight or less. The lower limit of the residual ratio is not particularly limited, and when the residual ratio decreases, the amount of PHA incorporated in the waste water increases, which is preferable, but conversely, there is a disadvantage that the production yield of PHA decreases, so that the production cost of PHA rather increases. Thus, the residual ratio is preferably 50% by weight or more, more preferably 60% by weight or more, still more preferably 70% by weight or more, and especially preferably 80% by weight or more.

The solid PHA contained in waste water may be PHA of primary particles accumulated in a microorganism, or PHA of granules formed by aggregation of the primary particles, or pellet-shaped PHA. The pellet-shaped PHA can be included in waste water discharged after PHA is molded into pellet shape in the molding step. PHA of primary particles is most preferable because the rates of the nitrification reaction and the denitrification reaction are easily improved. From the same point of view, the solid PHA is preferably small in size, and PHA contained in waste water preferably has a volume average particle size of 5000 µm or less, more preferably 1000 µm, still more preferably 500 µm or less, and most preferably 100 µm or less. For measurement of the volume average particle size, for example, Microtrac MT 3300 II manufactured by NIKKISO Co., Ltd. can be used.

Waste water containing nitrogen-containing impurities and PHA is most likely generated in a separation operation of separating the aqueous phase and solid PHA during the purification step. Here, the aqueous phase separated from PHA is discharged as waste water containing nitrogen-containing impurities and part of the PHA. Thus, control of the process yield in this separation operation facilitates control of the residual ratio. Here, the process yield in the separation operation is a ratio of the weight of PHA isolated in the separation operation to the weight of PHA contained in a PHA-containing aqueous suspension liquid before the separation operation is performed. The process yield in the separation operation is preferably 99.5% by weight or less, more preferably 98.5% by weight or less, and still more preferably 97.5% by weight or less for improving the nitrogen removal rate by incorporation of PHA in waste water. The lower limit of the process yield is not particularly limited, but is preferably 60% by weight or more, more preferably 70% by weight or more, and still more preferably 80% by weight or more so that the production yield of PHA does not decrease too much.

The specific means for separation operation for separating the aqueous phase from PHA is not particularly limited, and specific examples thereof include filtration devices having a compression function such as a filter press, a tube press, a plate press, a gauge press, a belt press, a screw press or a disc press; centrifugal settlers and centrifugal separators using a centrifugal force; and separation membranes. In addition, the separation operation may be performed using single means, or using a plurality of means in combination. The separation operation may be performed when PHA is in the form of primary particles, or after PHA is aggregated to increase the particle size. By adjusting conditions for performing the separation operation, adjustment can be easily made so that part of PHA is contained in the aqueous phase to be separated.

(Nitrogen Removal Step)

In the nitrogen removal step, waste water which is discharged from the discharge step and contains nitrogen-containing impurities and PHA is biologically treated to remove the nitrogen-containing impurities from the waste water. In biological treatment of waste water, the waste water is supplied to a treatment tank containing bacterial cells having a biodegradable resin decomposing ability, bacterial cells having a nitrification ability, and bacterial cells having a denitrification ability. A treatment tank (anaerobic treatment tank) containing bacterial cells having a nitrification ability and a treatment tank (aerobic treatment tank) containing bacterial cells having a denitrification ability may be separately provided, but according to the present invention, the nitrification reaction can be made to coexist with the denitrification reaction in one system, and therefore, in one wastewater treatment tank where bacterial cells having a biodegradable resin decomposing ability, bacterial cells having a nitrification ability, and bacterial cells having a denitrification ability coexist, the waste water can be treated. Here, a normal activated sludge treatment tank (aeration tank) can be used. This is because the above-mentioned microorganism group exists in a concentrated state in a normal activated sludge.

In removal of nitrogen according to the present invention, it is preferable to maintain a state in which oxygen is dissolved in waste water fed to the treatment tank. Thus, it is preferable to supply oxygen to waste water in the treatment tank, and it is more preferable that the concentration of dissolved oxygen in the waste water is kept a certain level or higher. The concentration of dissolved oxygen in waste water is preferably 1.5 ppm or more, and more preferably 2 ppm or more, from the viewpoint of the nitrogen removal rate. The upper limit of the concentration of dissolved oxygen is not particularly limited, but it is preferable to keep the concentration at a minimum necessary value from the viewpoint of cost considering that oxygen is forcibly supplied. Specifically, the concentration of dissolved oxygen is preferably 4 ppm or less, and more preferably 2.5 ppm or less. When oxygen is supplied, it is preferable to control the supplied amount of oxygen while monitoring the amount of oxygen online. As a method for forcibly supplying oxygen, it is possible to suitably use any method that can be conceived by those skilled in the art. For example, an oxygen supply system that is used for normal activated sludge treatment can be suitably used. To supply oxygen into waste water, air may be used or pure oxygen may be used.

As described above, it is preferable that the present invention is carried out under aerobic conditions, and even under aerobic conditions, the denitrification reaction, which is a reduction reaction, proceeds efficiently. This may be because PHA is decomposed by bacterial cells having biodegradable resin decomposing ability, the surroundings of PHA are thus partially brought into an anaerobic state, and PHA acts as a hydrogen donor on bacterial cells having a denitrification ability, so that the denitrification reaction proceeds efficiently even under aerobic conditions.

The temperature of waste water at the time of carrying out the present invention is not particularly limited, but a temperature condition suitable for a growth temperature of an involved microorganism is preferable. In general, the lower limit of the optimum temperature range is preferably 10 degrees Celsius or higher, more preferably 15 degrees Celsius or higher, and still more preferably 20 degrees Celsius or higher, and the upper limit temperature is preferably 60 degrees Celsius or lower, more preferably 55 degrees Celsius or lower, and still more preferably 50 degrees Celsius or lower, but the preferred temperature of waste water depends on an involved microorganism, and therefore is not limited thereto. In addition, since the nitrification reaction and the denitrification reaction have high dependency on temperature, it is preferable to carry out the present invention while controlling the temperature of waste water to the optimum temperature.

The pH of waste water at the time of carrying out the present invention is not particularly limited, but as with the temperature, a pH condition suitable for a growth pH of an involved microorganism is preferable. In general, the lower limit of the optimum pH range is preferably 3 or more, more preferably 4 or more, and still more preferably 5 or more, and the upper limit of the optimum pH range is preferably 10 or less, more preferably 9 or less, and still more preferably 8 or less, but the preferred pH of waste water depends on an involved microorganism, and therefore is not limited thereto. In addition, since the nitrification reaction and the denitrification reaction have high dependency on pH, it is preferable to carry out the present invention while controlling the pH of waste water to the optimum pH. A reagent to be used for adjusting the pH is not particularly limited, and it is possible to suitably use any reagent that can be conceived by those skilled in the art, such as sodium hydroxide or sulfuric acid.

When the nitrogen removal step is carried out as described above, the decomposition reaction of PHA as well as the nitrification reaction and denitrification reaction of nitrogen-containing impurities progresses in waste water, so that the nitrogen-containing impurities are reduced to nitrogen molecules, and released as a nitrogen gas from the waste water. As a result, the amount of nitrogen-containing impurities contained in the waste water can be reduced. In addition, in this process, PHA contained in the waste water is also decomposed, and therefore the amount of PHA in the waste water can also be reduced. Further, PHA remaining in the waste water can be aggregated or settled if necessary, and removed from the waste water.

EXAMPLES

Hereinafter, the present invention will be described in more detail by way of examples, but the present invention is in no way limited to these examples.

(Reference Example 1) Verification Taking Incorporation of PHA Primary Particles in Consideration First, 1 mM of citric acid, 2 mM of potassium dihydrogenphosphate, 0.5 mM of magnesium sulfate heptahydrate, 20 mM of sodium chloride, 0.02 mM of calcium chloride dihydrate, 0.01 mM of zinc sulfate heptahydrate, 0.03 mM of iron sulfate (II) heptahydrate, 0.01 mM of copper sulfate pentahydrate, 5 mg/L of EDTA and 20 mM of ammonium chloride were dissolved in distilled water. Sodium hydroxide with a concentration of 30% was added to perform pH adjustment so that the pH of the resulting solution was 8.5, and this solution was used as simulated waste water in the following experiments. The ratio (weight ratio) of the amount of soluble carbon to the amount of soluble nitrogen in the simulated waste water was 0.25.

Sludge was collected in mixture from an aeration tank, a nitrification tank and a denitrification tank of integrated waste water treatment equipment in a plant at Kaneka Corporation, the sludge was centrifuged at 3000 G for 10 minutes, and the supernatant was discarded to separate settled sludge. This settled sludge was mixed with distilled water in an amount equal to that of the discarded supernatant, and suspended. The suspended sludge was centrifuged at 3000 G for 10 minutes again, and the supernatant was discarded again to obtain washed sludge. The washed sludge was mixed with the simulated waste water prepared above, and resuspended to a concentration equal to that of the initial collected sludge to obtain a sludge suspension liquid. The concentration of ammonia nitrogen contained in the supernatant of the sludge suspension liquid was measured, and the result showed that the concentration was 280 mg/L.

To the sludge suspension liquid were added 3% by weight of PHBH primary particles (volume average particle size: 1 to 2 µm, 3 HH mol ratio: 11 mol %), and the mixture was aerated in an environment at 30±2° C. Here, the aeration was performed while the pH was adjusted using sodium hydroxide with a concentration of 30% so that the pH of the sludge suspension liquid fell within a range of 8 to 8.5, and while the aeration amount was adjusted so that the concentration of dissolved oxygen (Do) of the sludge suspension liquid was 5 ppm or more.

A sample was collected from the sludge suspension liquid after elapse of a predetermined time after the start of aeration, the sample was centrifuged at 9000 G for 10 minutes, and the concentrations of ammonia nitrogen, nitrite nitrogen and nitrate nitrogen were measured for the resulting supernatant. For measurement of the concentrations of ammonia nitrogen, nitrite nitrogen and nitrate nitrogen, DR 6000 manufactured by HACH Company and corresponding reagents (TNT 832, TNT 835 and TNT 840) were used.

Figure 2:
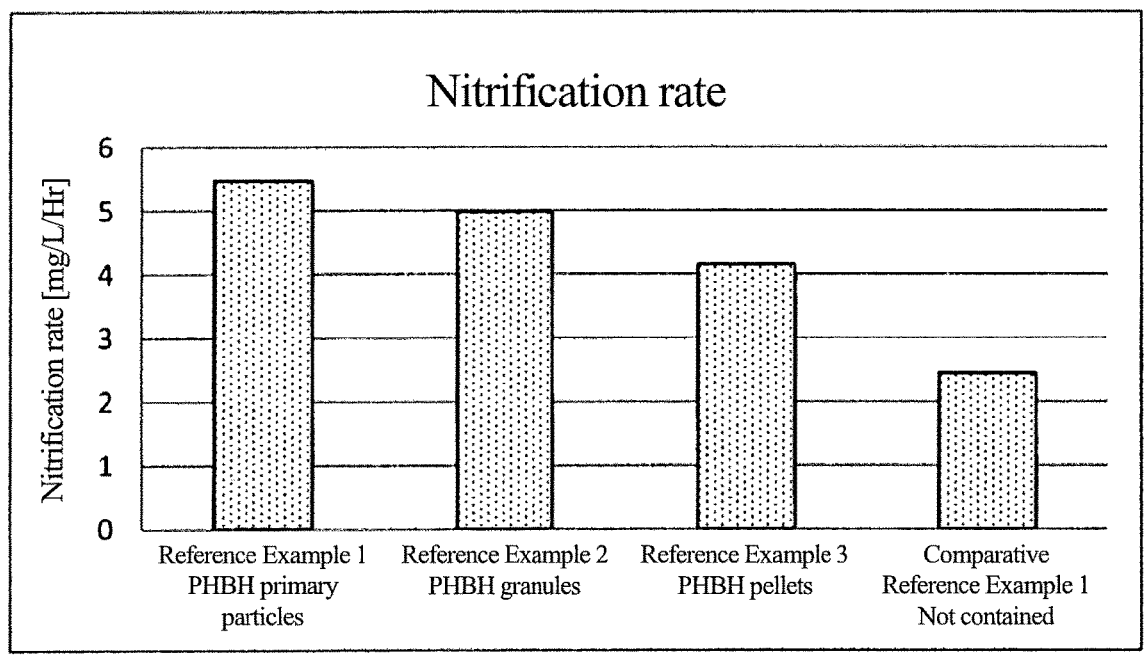
FIG. 2 illustrates graphs showing a nitrification rate in the system for Reference Example 1-3 and Comparative Reference Example 1.

The nitrogen removal rate was calculated from a time-dependent change in the sum of the concentrations of ammonia nitrogen, nitrite nitrogen and nitrate nitrogen. The results are shown in FIG. 1. The nitrification rate was calculated from a time-dependent change in concentration of ammonia nitrogen. The results are shown in FIG. 2. The rates were calculated in the following manner: the start of aeration was set to 0 hour, the concentration was measured at 0 hour, after 10 hours, after 20 hours, after 30 hours and after 40 hours, and the rate was calculated from a gradient obtained by the least squares method using the measured values of the concentrations.

(Reference Example 2) Verification Taking Incorporation of PHA Granules in Consideration In accordance with the description of Reference Example 1, a sludge suspension liquid was prepared in which washed sludge was suspended with simulated waste water, and in place of PHBH primary particles, PHBH granules (volume average particle size: 100 to 350 µm, 3 HH mol ratio: 11 mol %) were added thereto in the same amount as in Reference Example 1. The mixture was aerated, and the respective nitrogen concentrations were measured with time. The other experiment conditions and analysis conditions were in accordance with the method described in Reference Example 1. The nitrogen removal rate and the nitrification rate were calculated in the same manner as in Reference Example 1. The results thereof are shown in FIGS. 1 and 2.

(Reference Example 3) Verification Taking Incorporation of PHA Pellets in Consideration In accordance with the description of Reference Example 1, a sludge suspension liquid was prepared in which washed sludge was suspended with simulated waste water, and in place of PHBH primary particles, PHBH pellets (circular column shape having a diameter of 3 mm and a height of 3 mm, 3 HH mol ratio: 11 mol %) were added thereto in the same amount as in Reference Example 1. The mixture was aerated, and the respective nitrogen concentrations were measured with time. The other experiment conditions and analysis conditions were in accordance with the method described in Reference Example 1. The nitrogen removal rate and the nitrification rate were calculated in the same manner as in Reference Example 1. The results thereof are shown in FIGS. 1 and 2.

Comparative Reference Example 1

In accordance with the description of Reference Example 1, a sludge suspension liquid was prepared in which washed sludge was suspended with simulated waste water, and was aerated without adding PHA of PHBH primary particles or the like, and the respective nitrogen concentrations were measured with time. The other experiment conditions and analysis conditions were in accordance with the method described in Reference Example 1. The nitrogen removal rate and the nitrification rate were calculated in the same manner as in Reference Example 1. The results thereof are shown in FIGS. 1 and 2.

From the results shown in FIG. 1, it is apparent that in Reference Examples 1 to 3 where the sludge suspension liquid contained PHA primary particles, PHA granules or PHA pellets, both the nitrogen removal rate and the nitrification rate were improved as compared to Comparative Reference Example 1 where the sludge suspension liquid did not contain PHA at all. Therefore, it is apparent that when waste water contains PHA, the nitrification reaction and the denitrification reaction easily proceeds concurrently in waste water, so that nitrogen components contained in the waste water can be efficiently removed. Since the nitrogen removal rate improves, it is possible to downsize the treatment tank in waste water treatment equipment by incorporation of PHA in waste water.

(Example 1) Verification Using Actual Waste Water

Verification was conducted using actual waste water generated in the PHA production step. As the actual waste water used for the verification, an aqueous phase discharged in the separation step of separating the PHA and the aqueous phase containing impurities other than the PHA was used. Specifically, waste water was used which was obtained by adjusting the retention time and/or centrifugal acceleration in centrifugation for adjusting the amount of PHBH contained in waste water in the step of recovering PHBH by separating PHBH and the aqueous phase through centrifugation from the PHBH suspension liquid obtained by the method described in paragraphs [0048] to [0050] in WO 2010/067543. The residual ratio of PHBH in the separation step at that time was 98.5% by weight.

For calculating the amount of PHBH contained in the used actual waste water, the actual waste water was centrifuged at 10000 G for 10 minutes, and PHBH contained in the actual waste water was recovered. The recovered PHBH was washed with alkaline water having a pH of 11 at a plurality of times, and then dried, and the amount of PHBH was confirmed. As a result, it was confirmed that the actual waste water used for verification contained about 1% by weight of PHBH. The 3 HH mol ratio of the PHBH was 6 mol %.

On the other hand, sludge was collected in mixture from an aeration tank, a nitrification tank and a denitrification tank of integrated waste water treatment equipment in a plant at Kaneka Corporation, the sludge was centrifuged at 3000 G for 10 minutes, and the supernatant was discarded to separate settled sludge. This settled sludge was mixed with distilled water in an amount equal to that of the discarded supernatant, and suspended. The suspended sludge was centrifuged at 3000 G for 10 minutes again, and the supernatant was discarded again to obtain washed sludge. The washed sludge was mixed with the actual waste water, and resuspended to a concentration equal to that of the initial collected sludge to obtain a sludge suspension liquid.

Figure 3:
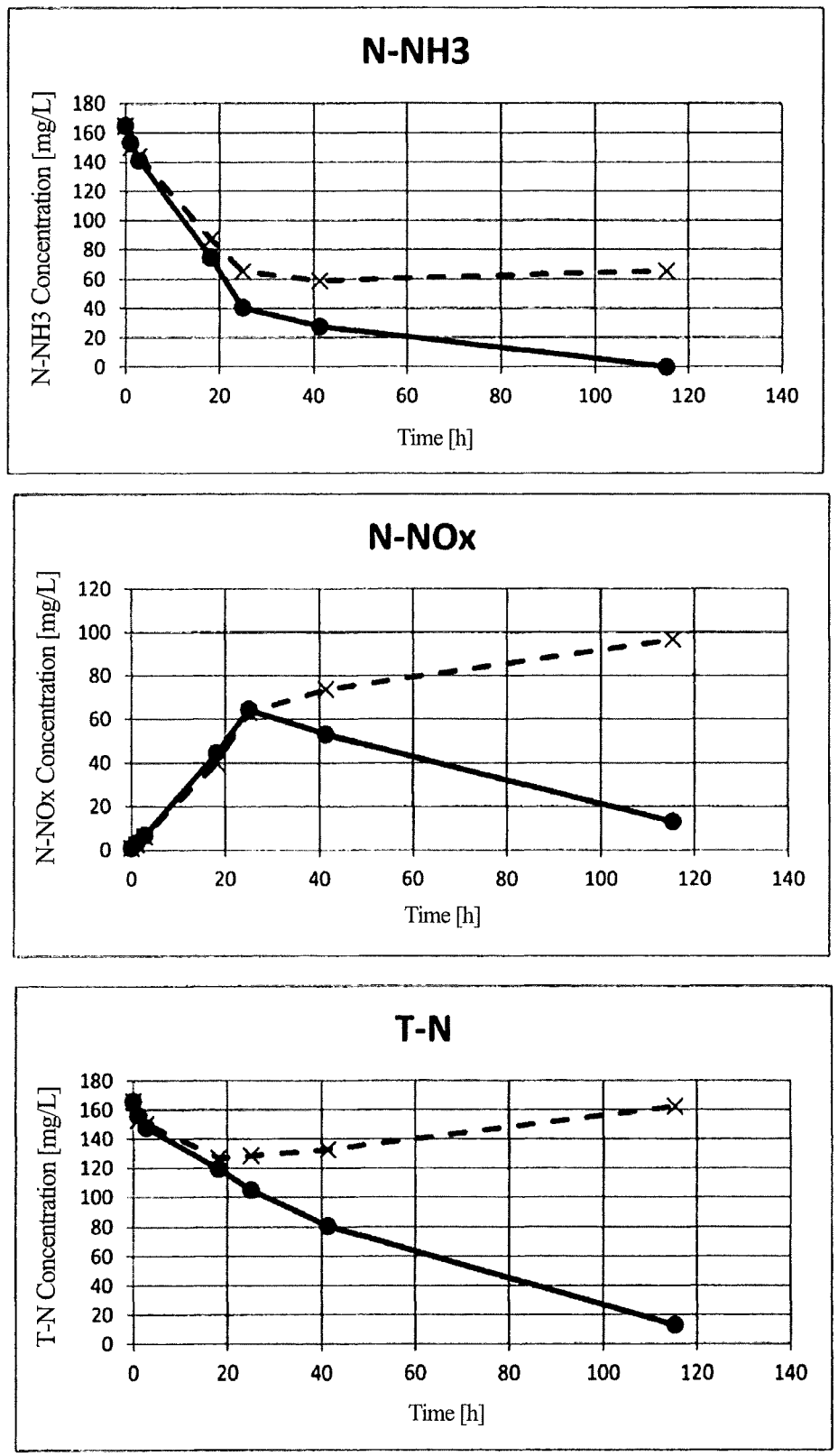
FIG. 3 illustrates graphs showing a time-dependent change in ammonia nitrogen concentration (N—NH$_3$), a time-dependent change in the sum of a nitrite nitrogen concentration and a nitrate nitrogen concentration (N-NOx) and a time-dependent change in total nitrogen concentration (T-N) in the system for Example 1 and Comparative Example 1.

The sludge suspension liquid was aerated while the aeration amount was adjusted so that the concentration of dissolved oxygen (DO) was 5 ppm or more. Sampling was performed with time, and the respective nitrogen concentrations were measured. The aeration conditions and measurement method were in accordance with the method described in Reference Example 1. The results are shown with solid lines in FIG. 3. In FIG. 3, N—NH$_3$ represents the concentration of ammonia nitrogen, N-NOx represents the sum of the concentrations of nitrite nitrogen (N—NO$_2$) and nitrate nitrogen (N—NO$_3$), and T-N (total nitrogen) represents the sum of the concentrations of ammonia nitrogen, nitrite nitrogen and nitrate nitrogen.

Comparative Example 1

The actual waste water used in Example 1 was centrifuged at 10000 G for 10 minutes to remove PHBH from the actual waste water. A sludge suspension liquid was obtained in the same manner as in Example 1 except that waste water which did not contain the PHBH was used in place of the actual waste water in Example 1. The sludge suspension was aerated, and the nitrogen concentration was measured with time. The results are shown with broken lines in FIG. 3.

From the results shown in FIG. 3, it is apparent that in Example 1 where waste water containing PHBH was biologically treated, the concentration of ammonia nitrogen (N—NH$_3$), the sum of the concentrations of nitrite nitrogen and nitrate nitrogen (N-NOx), and the total nitrogen concentration (T-N) each considerably decreased with time as compared to Comparative Example 1 where waste water which did not contain PHBH was biologically treated.

In particular, in Comparative Example 1, the sum of the concentrations of nitrite nitrogen and nitrate nitrogen (N-NOx) increases with time, and the total nitrogen concentration (T-N) hardly decreases, whereas in Example 1, it is noticeable that the sum of the concentrations of nitrite nitrogen and nitrate nitrogen (N-NOx) temporarily increases, but turns to decrease thereafter, and the total nitrogen concentration (T-N) continues to decrease consistently. This shows that in Example 1, the nitrification reaction coexists with the denitrification step.

From the results described above, it has been demonstrated that when waste water generated in the PHA production process is caused to contain PHA, nitrogen components contained in the waste water can be efficiently removed.

The invention claimed is:

1. A method for producing polyhydroxyalkanoic acid, the method comprising:
   purifying or molding polyhydroxyalkanoic acid biosynthesized in bacterial cells of a microorganism;
   discharging waste water produced during the purifying or molding, the waste water comprising nitrogen-containing impurities; and
   biologically treating the waste water to remove the nitrogen-containing impurities from the waste water,
   wherein a ratio of a weight of the polyhydroxyalkanoic acid obtained by the purifying or the molding to a weight of the polyhydroxyalkanoic acid biosynthesized in the bacterial cells is 99% by weight or less, and
   the waste water that is biologically treated comprises the polyhydroxyalkanoic acid in addition to the nitrogen-containing impurities.

2. The method according to claim 1, wherein the purifying or molding comprises disrupting the microorganism containing biosynthesized polyhydroxyalkanoic acid by a physical, chemical or biological method and decomposing and/or removing impurities other than the polyhydroxyalkanoic acid to purify the polyhydroxyalkanoic acid.

3. The method according to claim 1, wherein the nitrogen-containing impurities comprise a water-soluble or water-dispersible component formed by decomposing a protein, a lipid or a nucleic acid derived from the microorganism during the purifying.

4. The method according to claim 1, wherein in the discharging, the polyhydroxyalkanoic acid contained in the waste water has a volume average particle size of 5000 μm or less.

5. The method according to claim 1, wherein the waste water that is biologically treated comprises dissolved oxygen in an amount of 1.5 ppm or more.

6. The method according to claim 1, wherein the waste water that is biologically treated has a temperature of 10 degrees Celsius or higher and 60 degrees Celsius or lower.

7. The method according to claim 1, wherein the waste water that is biologically treated has a pH of 3 or more and 10 or less.

8. The method according to claim 1, wherein the ratio of the weight of the polyhydroxyalkanoic acid obtained by the purifying or the molding to the weight of the polyhydroxyalkanoic acid biosynthesized in the bacterial cells is 50 to 98% by weight.

9. The method according to claim 1, wherein the ratio of the weight of the polyhydroxyalkanoic acid obtained by the purifying or the molding to the weight of the polyhydroxyalkanoic acid biosynthesized in the bacterial cells is 60 to 97% by weight.

10. The method according to claim 1, wherein in the discharging, the polyhydroxyalkanoic acid contained in the waste water has a volume average particle size of 100 μm or less.

11. The method according to claim 1, wherein the waste water that is biologically treated comprises dissolved oxygen in an amount of 2 to 4 ppm.

12. The method according to claim 1, wherein the waste water that is biologically treated has a temperature of 15 degrees Celsius or higher and 55 degrees Celsius or lower.

13. The method according to claim 1, wherein the waste water that is biologically treated has a pH of 4 or more and 9 or less.

14. The method according to claim 1, wherein the polyhydroxyalkanoic acid is at least one selected from the group consisting of 3-hydroxybutyrate, 4-hydroxybutyrate, 3-hydroxyhexanonate, 3-hydroxypropionate, 3-hydroxyvalerate, 3-hydroxyhexanoate, 3-hydroxyheptanoate, and 3-hydroxyoctanoate.

15. The method according to claim 1, wherein the biological treating of the waste water comprises contacting the waste water with bacterial cells capable of decomposing biodegradable resin, bacterial cells having a nitrification ability, or bacterial cells having a denitrification ability.

* * * * *